United States Patent [19]
Golubev et al.

[11] Patent Number: 6,015,566
[45] Date of Patent: *Jan. 18, 2000

[54] PEPTIDE COMPOSITION GENERATING AN IMMUNE RESPONSE AGAINST HERPES VIRUS

[75] Inventors: Daniel B. Golubev, Jackson Heights, N.Y.; Alexander Chaihorsky, Reno, Nev.

[73] Assignee: Bio-Virus Research Incorporated, Sparks, Nev.

[*] Notice: This patent is subject to a terminal disclaimer.

[21] Appl. No.: 09/088,154

[22] Filed: Jun. 1, 1998

Related U.S. Application Data

[63] Continuation-in-part of application No. 08/708,893, Sep. 5, 1996, Pat. No. 5,760,175.

[51] Int. Cl.[7] .................. A61K 39/245; A61K 39/12; C07H 21/04
[52] U.S. Cl. .................. 424/229.1; 424/186.1; 424/188.1; 530/324; 536/23.72
[58] Field of Search .................. 424/229.1, 186.1, 424/188.1; 530/324; 536/23.72

[56] References Cited

U.S. PATENT DOCUMENTS 5,502,036  3/1996  Adams et al. .................. 514/17
5,760,175  6/1998  Golubev et al. .................. 530/324

OTHER PUBLICATIONS

Arnon et al. The FASEB Journal, 1992, vol. 6, pp. 3265–3274, Nov. 1992.

*Primary Examiner*—Chris Eisenschenk
*Assistant Examiner*—Ali R. Salimi
*Attorney, Agent, or Firm*—Herbert Dubno; Jonathan Myers

[57] ABSTRACT

A composition is disclosed for generating an immune response against a herpes virus in an animal subject susceptible thereto, wherein the vaccine comprises a compound of the Formula:

```
Val Asn Pro Arg Gly Gly Cys Phe Leu Gly Gly Gly
 1            5                      10
Ala Lys Ala Gly
         15
Gly Gly Gly Gly Arg Ala Ala Gly Gln Pro Arg Ala
         20                  25
``` designated Sequence ID 1. The composition is especially effective in generating an immune response against Kaposi's sarcoma herpesvirus.

6 Claims, No Drawings

PEPTIDE COMPOSITION GENERATING AN IMMUNE RESPONSE AGAINST HERPES VIRUS

CROSS REFERENCE TO RELATED APPLICATIONS

This application is a continuation-in-part of U.S. patent application Ser. No. 08/708,893 filed Sep. 5, 1996 now U.S. Pat. No. 5,760,175.

FIELD OF THE INVENTION

The present invention relates to a vaccine against herpes virus for the treatment and prevention of several herpes virus infections. More particularly the invention relates to a vaccine against Kaposi's Sarcoma-Associated Herpes Virus (KS'HV) containing a new peptide encoded by parts of herpes virus KNA homologous to subunits of KS'HV.

BACKGROUND OF THE INVENTION

Kaposi's Sarcoma is a condition characterized by malignant skin tumors. Kaposi's Sarcoma has been recognized since the middle of the nineteenth century as a specific disease. In the past Kaposi's Sarcoma has developed slowly and was seen almost exclusively in elderly Italian and Jewish men. However, since 1981 Kaposi's Sarcoma has been a prominent feature of AIDS. In patients with AIDS, Kaposi's Sarcoma is highly aggressive and tumors soon become wide-spread.

The tumors, consisting of blue-red nodules, usually start on the patient's feet or ankles, spread further up the legs and then appear on the patient's hands and arms. In patients with AIDS these tumors commonly affect the gastrointestinal and respiratory tracts, where these tumors may cause severe internal bleeding. In fact as an immediate cause of death in patients suffering from AIDS in the U.S.A., Kaposi's Sarcoma is second only to pneumonia induced by *Pneumocista Karinii*.

Until recently Kaposi's Sarcoma was evaluated as a disease associated only with patients suffering from a compromised immunosystem. But in 1995 Dr. Patrick Moore of Columbia University recognized some specific herpes virus sequences in tissues obtained from patient's suffering from Kaposi's Sarcoma. Then Dr. Don Ganem of the University of California isolated from the patient's tumorous tissues, a specific herpes virus which is the etiological agent of the Kaposi's Sarcoma. The disease's etiological factor is activated by the immunodefective status of the AIDS patient.

OBJECTS OF THE INVENTION

It is an object of the invention to provide a vaccine as a prophylaxis against pathogenic development of several herpes infections, especially Kaposi's Sarcoma-Associated Herpes Virus (KS'HV).

SUMMARY OF THE INVENTION

We have found a vaccine composition that is effective against the pathogenic development of a number of herpes viruses, including Kaposi's Sarcoma-Associated Herpes Virus (KS'HV). The vaccine composition contains as active ingredient, a therapeutically effective amount of a new peptide of the Formula:

```
Val Asn Pro Arg Gly Gly Cys Phe Leu Gly Gly Gly
 1               5                      10

Ala Lys Ala Gly
        15

Gly Gly Gly Gly Arg Ala Ala Gly Gln Pro Arg Ala
        20                      25
``` designated as Sequence ID 1 in combination with a pharmaceutically acceptable inert vaccine carrier such as normal saline or a physiological oil (e.g. corn oil, sunflower oil).

The composition is prepared by incorporating the peptide having Sequence ID 1 in the pharmaceutically acceptable inert vaccine carrier such as normal saline or a physiological oil in an adequate concentration of said peptide. Preferably there is present 1.0 to 100 micrograms of the peptide per ml of pharmaceutical composition.

Since the peptide having Sequence ID 1 is itself a new compound, the new compound per se is considered part of the present invention as well.

Also contemplated to be within the scope of the invention is a method of prophylaxis of pathogenic development of several herpes virus infections, especially Kaposi's Sarcoma-Associated Herpes Virus (KS'HV), which comprises the step of administering to an animal subject, especially a mammalian subject, including man, a therapeutically effective amount of the pharmaceutical composition containing the peptide having Sequence ID. The herpes infections whose development can be prevented especially includes Kaposi's Sarcoma-Associated Herpes Virus (KS'HV), but also includes Herpes Simplex Virus I (HSV-1), Herpes Simplex Virus II (HSV-2), Human Cytomegalovirus (HCMV), Varicella Zoster Virus (VZV), Marek's Disease Virus (MDV) and Epstein-Barr Virus (EBV).

The compositions may preferably be administered to a mammalian subject parenterally, such as by injection. More preferably the compositions are administered by subcutaneous, intramuscular, intra-arterial, intravenous, or intradermal injection. A preferred dosage of the composition is 1 ml every 20 days administered in a series of 6 intramuscular injections. The full cycle of treatment may consist of 2 or 3 such courses with a 3 month interval in between.

Use of an adjuvant, for instance inorganic gels, such as alum, aluminum hydroxide, or aluminum phosphate that increase antigenic response, is optional in the compositions.

PREPARATION OF THE VACCINE AGAINST PATHOGENIC DEVELOPMENT OF HERPES INFECTIONS

The vaccine may be prepared by automated solid phase synthesis. When preparing the vaccine by recombinant DNA techniques, the following steps are employed:

Solid Phase Synthesis of the Peptide

The peptide having the Sequence ID 1 was synthesized using Automated Solid Phase Synthesis followed by purification using High Performance Liquid Chromatography (HPLC). See AminoTech 1991, Biochemical Reagents for Peptide Synthesis, AminoTech, Nepean, Ontario.

The resulting peptide having Sequence ID 1 was characterized by amino acid analysis (See Table 1) and sequence analysis (See Table 2). The results show that compound and structure of the synthetic peptide was identical to our specifications.

TABLE 1

FINAL REPORT OF AMINO ACID ANALYSIS REPORT
Sample #: 9506-303

| Residues | Expected Composition | Detected Composition |
|---|---|---|
| D/N | 1 | 1.08 |
| T | | |
| S | | |
| E/Q | 1 | 0.92 |
| P | 2 | 2.15 |
| G | 11 | 11.89 |
| A | 5 | 5.3 |
| C | 1 | 0.93 |
| V | 1 | 1.05 |
| M | | |
| I | | |
| L | 1 | 1.06 |
| Y | | |
| F | 1 | 0.92 |
| H | | |
| K | 1 | 0.92 |
| R | 3 | 2.89 |
| W | | N/A |

*The peptide was hydrolyzed for one hour with 6N HCl containing 0.1% phenol at 160° C.
**The cospoaition of the peptide was analyzed on a reverse-phase HPLC column.
N/A: The amino acid was destroyed by hydrolysis.

TABLE 2

CUSTOM PEPTIDE SYNTHESIS SHEET

CUSTOMER #:
CUSTOMER P.O. #: TAN/94/1
INVOICE #: 9506-303p
PRODUCT #: 9506-303
DESCRIPTION OF SEQUENCE: Seq. ID 1
* AMOUNT OF CRUDE PEPTIDE: mg
** AMOUNT OF >70% PURE PEPTIDE: mg,
*** AMOUNT OF HPLC-PURIFIED PEPTIDE: 25 mg (10 mg for immunization)
MASS SPECTROMETRY ANALYSIS:
DELIVERY DATE: 6-20-95
APPROVED BY: K.T.
REMARK: Store the product at −20° C.

* The crude peptide is machine grade synthesized by Tan Lab. peptide synthesis system using Fmac chemistry and purified by using multiple steps of ether precipitation. The peptide purity and sequence accuracy are highly depended on peptide length and sequences. This grad peptides are generally sufficient for initial screening studies.
** The peptide's synthesized under monitor for each coupling. Insufficient coupling will be recouped in unlimited times. The purity is checked by HPLC a absorbance 226.
*** The peptide is synthesized with monitor and purified by HPLC column. In general, the HPLC purified peptide should be at 85–95% purity (analyzed by HPLC at 225). It is sufficient for in vivo or in vitro and specific peptide antibody production.

Determination of Immunogenic Activity of the Peptide Vaccine

1. Coupling Peptides to Protein Carriers with Glutaraldehyde

Glutaraldehyde is a bifunctional coupling agent that complexes amino groups on the peptide with amino groups on human serum albumin (HSA). For preparing a complex of peptide-HSA with glutaraldehyde, it is necessary to carry out the following procedures:

(1) 20 mM glutaraldehyde (0.4 ml 50% glutaraldehyde+ 99.6 ml H20) were prepared;
(2) HSA (2.0 mg/0.5 ml 0.01 M phosphate, pH 7.5) was dissolved in water;
(3) 4.0 mg of peptide were added to 0.5 ml water;
(4) The glutaraldehyde (0.33 ml 20 mM) was added dropwise with stirring to the water over the course of 5 minutes at room temperature. Stirring of the solution was continued for another 30 minutes. The solution became yellow.
(5) Glycine (0.1 ml 1M) was then added to the solution to block any unreacted glutaraldehyde and allowed to remain for 30 minutes;
(6) Excess peptide and reagent were then removed by either exhaustive dialysis in phosphate-buffered saline (see Kagan & Glick 1979). "Oxyitocin", Methods of Hormone Radioimmunoassay. B. B. Jaffe & H. R. Behrman, eds, pp 328 to 329, Academic Press, NY).

2. Immunization of Rabbits on the Basis of a Special Schedule of Injections by the peptide coupled to HSA:

Immunization of two rabbits was carried out according to the following immunization schedule:

day 1, base blood samples, first injection;
day 8, second injection;
day 24, third injection;
day 40, fourth injection;
day 55, fifth injection;
day 70, second and final blood samples.

The immunization dose was 0.5 mg per injection.

3. ELISA Titration of Rabbit's Immunosera with Synthetic Peptides

The antibody level in the post-immunization sera was tested using the basic Enzyme Linked Immunosorbent Assay (ELISA) method.

As is known, ELISA can be used for quantification of either antigens or antibodies in several patient specimens, especially in sera. Its action is based on the competition for a specific antibody binding site. A labelled (the control or known) antigen or antibody competes with that from the patient, the unlabelled or unknown antibody, for access to the binding site.

In this case, to measure the antibodies in a rabbit's post-immunization sera, each of the known herpes virus antigens (listed hereinbelow) was fixed to a special plastic microplate, incubated with the test serum (at dilutions of 1:30,000, 1:10,000; 1:3,000; and 1:1000), washed, and then reincubated with an anti-immunoglobulin labeled with an enzyme, such as horseradish peroxidase.

The amount of antibody bound is proportional to the enzyme's activity, so assaying for the enzyme activity, and thus bound antibody, can be done by adding the enzyme's substrate. Enzyme activity was measured by adding the substrate and estimating the resulting color, representing activity, with a spectrophotometer. Consistent with the principles of the assay, the ELISA titration method requires some specific procedures:

1. Coat a 96-well plate with 20 micrograms/ml of the specified known herpes virus antigen in 0.01 M sodium phosphate buffer at pH 7.2 containing 0.1M NaCl(PBS) (50 microl/well, 4 overnight).
2. Wash twice with PBS, then block the wells with TANA's blocking solution for one hour at 37° C.
3. Incubate the wells with diluted serum (using 1.0% BSA/PBS for dilution) at 37° C. for 2 tom 4 hours.
4. Wash four times with PBS, then incubate with 1:3,000 diluted goat anti-rabbit IgH-horseradish conjugate (TANA Laboratories using 1.0% BSA/PBS for dilution) for 1 hour.
5. Wash four times with PBS, then incubate with TANA's colorimetric ELISA substrate (tetramethylbenzene/ $H_2O_2$ solution).

6. Stop the enzyme reaction with TANA's ELISA-stopping buffer (diluted phosphoric acid).

7. Read the plate using 450 nm ultra-violet light.

As antigens for the ELISA titration the following samples of virus-infected cells were used:

1. Hep-2 TC, infected by HSV-1 (patent strain) (ATCC VR-733),
2. Hep-2 TC, infected by HSV-2 (patent strain) (ATCC VR-734),
3. Human diploid fibroblast cells, infected by HCMV, strain Ad-169 (ATCC VR 538),
4. Human Lymphoblastoid Cells, infected by EBV-Burkitt's Lymphoma Agent (ATCC VR 602),
5. MRC-5 cells, infected by VZV (strain ELLEN) ATCC VR 1367),
6. CEF-cells, infected by MDV (patent strain SB-1) (ATCC VR 2001),
7. Human cord blood lymphocytes, infected by HHV6 (strain Z-29) (ATCC VR 1348),
8. Human cord blood lymphocytes, infected by HHV7 (strain SB ATCC VR 1348),
9. Lymphoma cells, produced Kaposi's sarcoma-associated herpesvirus (KS'HV) (BC-1) (ATCC CRL 2230).

The results of the ELISA titration for determination of the titer of antibodies against several members of the above-mentioned herpesvirus family after immunization of rabbits with the peptide having Sequence ID 1 is presented as follows:

| Herpes Virus | Antibody Titer Against |
|---|---|
| HSV1 | 1:300 |
| HSV2 | 1:300 |
| HHV6 | — |
| HHV7 | — |
| HCMV | 1:3000 |
| VZV | 1:3000 |
| EBV | 1:300 |
| MDV | 1:3000 |
| KS'HV | 1:3000. |

What is claimed is:

1. A pharmaceutical composition for generating an immune response to a herpes virus which comprises an effective amount of a compound comprising Sequence ID 1 coupled through a coupling agent to a pharmaceutically acceptable protein carrier.

2. The pharmaceutical composition for generating an immune response as defined in claim 1 wherein the herpes virus is Kaposi's Sarcoma.

3. The pharmaceutical composition for generating an immune response as defined in claim 1 wherein the coupling agent is glutaraldehyde.

4. The pharmaceutical composition for generating an immune response as defined in claim 1 wherein the pharmaceutically acceptable protein carrier is human serum albumin.

5. A method of generating an immune response to a herpes virus in a mammalian subject which comprises the step of administering to said subject an effective amount of the pharmaceutical composition defined in claim 1.

6. The method of generating an immune response as defined in claim 5, wherein the herpes virus is Kaposi's Sarcoma.

\* \* \* \* \*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

```
Val Asn Pro Arg Gly Gly Cys Phe Leu Gly Gly Gly Ala Lys Ala Gly
1               5                   10                  15

Gly Gly Gly Gly Arg Ala Ala Gly Gln Pro Arg Ala
            20                  25
```